(12) United States Patent
Fuchs

(10) Patent No.: US 6,997,357 B2
(45) Date of Patent: Feb. 14, 2006

(54) DISCHARGE DEVICE FOR AT LEAST ONE MEDIUM

(75) Inventor: Karl-Heinz Fuchs, Radolfzell (DE)

(73) Assignee: Ing. Erich Pfeiffer GmbH, Radolfzell (DE)

( * ) Notice: Subject to any disclaimer, the term of this patent is extended or adjusted under 35 U.S.C. 154(b) by 0 days.

(21) Appl. No.: 10/815,598

(22) Filed: Apr. 1, 2004

(65) Prior Publication Data

US 2004/0195276 A1 Oct. 7, 2004

(30) Foreign Application Priority Data

Apr. 3, 2003 (DE) ................................ 103 15 936

(51) Int. Cl.
*B67D 5/42* (2006.01)

(52) U.S. Cl. ................... 222/386; 222/83; 222/83.5; 222/145.5; 206/222

(58) Field of Classification Search ............... 222/386, 222/83, 145.5, 83.5, 88; 206/219–222, 568
See application file for complete search history.

(56) References Cited

U.S. PATENT DOCUMENTS

| | | | | |
|---|---|---|---|---|
| 3,735,900 A * | 5/1973 | Gores | ......................... | 222/129 |
| 4,031,892 A * | 6/1977 | Hurschman | .................. | 604/416 |
| 4,581,016 A * | 4/1986 | Gettig | .......................... | 604/88 |
| 4,886,495 A * | 12/1989 | Reynolds | ...................... | 604/88 |
| 5,171,219 A * | 12/1992 | Fujioka et al. | ................ | 604/82 |
| 5,352,196 A * | 10/1994 | Haber et al. | .................. | 604/90 |
| 5,692,644 A * | 12/1997 | Gueret | ......................... | 222/80 |
| 5,909,753 A * | 6/1999 | Rossi et al. | .................. | 141/330 |
| 6,305,576 B1 * | 10/2001 | Leoncavallo | ............... | 222/83.5 |
| 6,332,721 B1 * | 12/2001 | Inokuchi | ...................... | 385/93 |
| 6,474,861 B1 * | 11/2002 | De Laforcade | ............. | 366/130 |
| 6,626,379 B1 | 9/2003 | Ritsche et al. | | |
| 6,655,525 B1 * | 12/2003 | Song | .......................... | 206/222 |

FOREIGN PATENT DOCUMENTS

| | | |
|---|---|---|
| DE | 197 49 514 | 5/1999 |
| DE | 101 30 965 | 1/2003 |

* cited by examiner

*Primary Examiner*—Frederick Nicolas
(74) *Attorney, Agent, or Firm*—Flynn, Thiel, Boutell & Tanis, P.C.

(57) ABSTRACT

A discharge device for at least one medium has at least two media reservoir sections positioned rigidly relative to one another and which pass into one another in their interior through a step shoulder. The reservoir sections are formed by two separate hollow bodies that are superimposed over a portion of their length and are tightly interconnected.

18 Claims, 2 Drawing Sheets

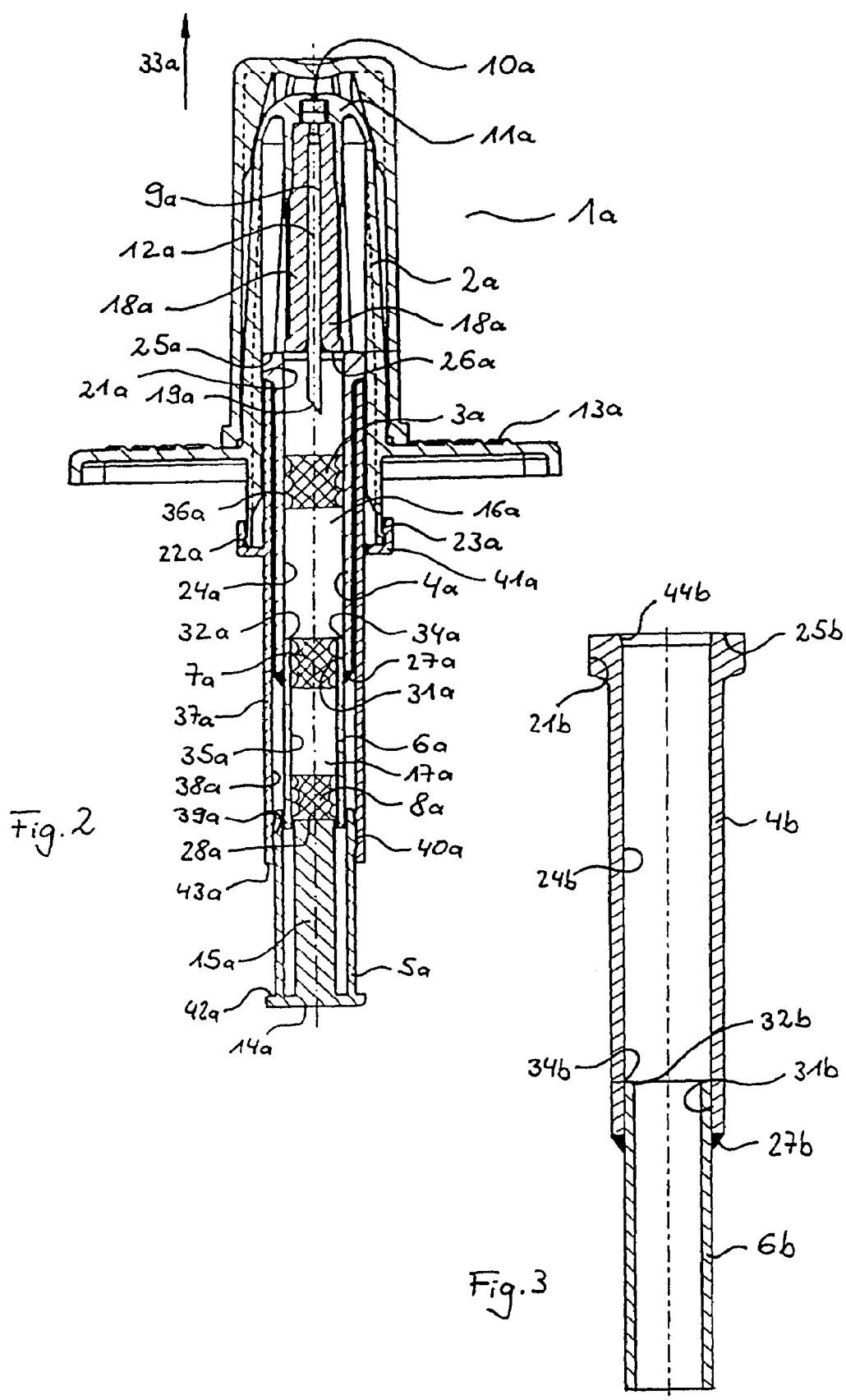

DISCHARGE DEVICE FOR AT LEAST ONE MEDIUM

Figure 1:
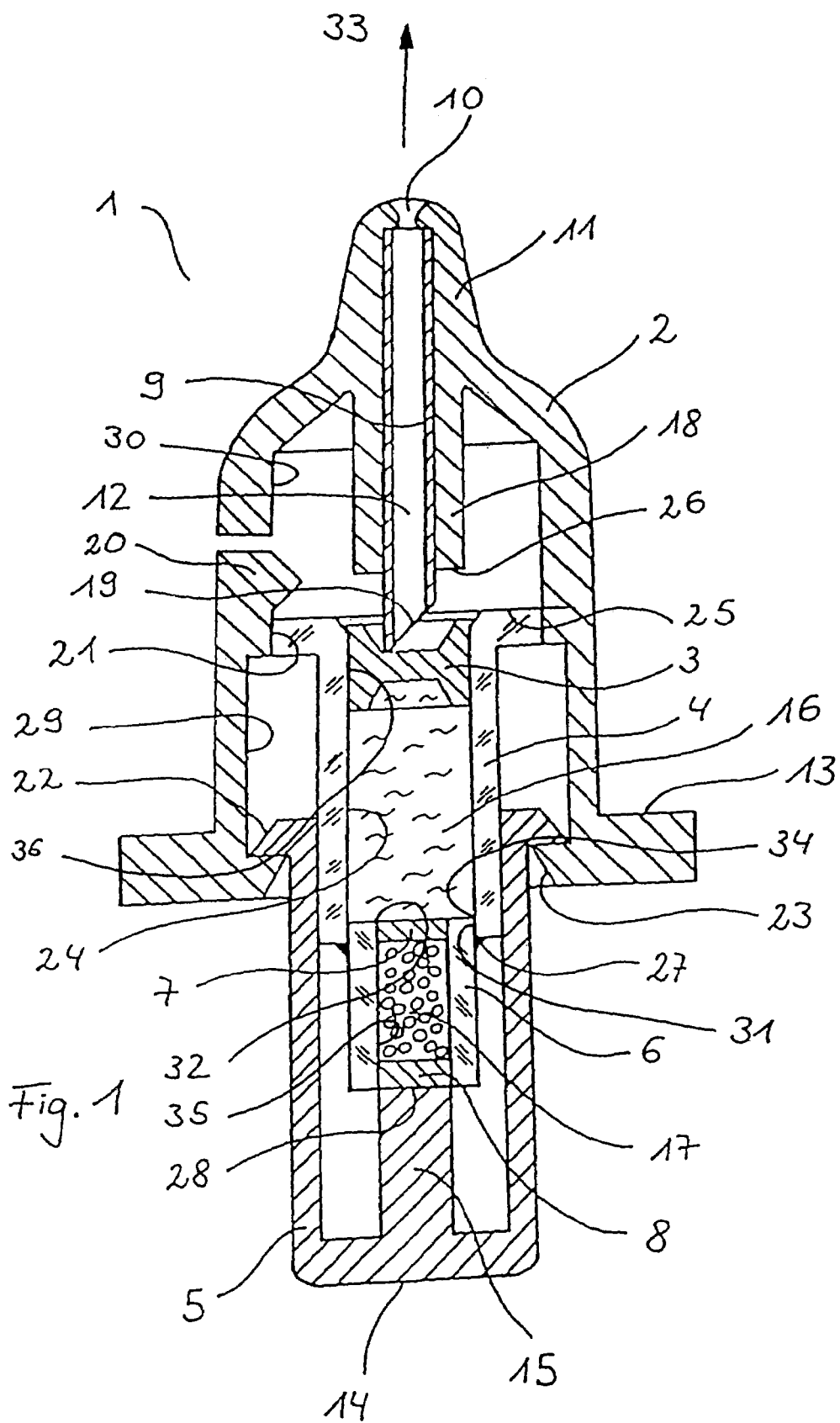

The invention relates to a discharge device for at least one medium, with a medium reservoir, a pumping device and a discharge opening.

Numerous different constructions of such discharge devices are known from the prior art. A discharge of one or more media, particularly pulverized solids, liquids with an aqueous to viscous consistency or gases, is of great importance in particular in numerous cosmetic and pharmaceutical sectors. The at least one medium is stored in a medium reservoir of the discharge device and can be conveyed by a pumping device from the medium reservoir through a discharge opening into the environment. The discharge opening is matched to the viscosity and intended use of the medium to be discharged. More particularly for media with a small particle size, aqueous consistency and low viscosity, frequently an atomization in the ambient air by means of a nozzle-shaped outlet port is sought. For semiliquid, highly viscous liquids a cylindrical or conical discharge opening is preferred. The pumping devices for discharging a medium from the media reservoir can be designed as a self-priming pump, where the pressure necessary for discharge purposes is built up in the pumping device outside the media reservoir. Other pumping devices place the media reservoir under pressuring using appropriate means and consequently bring about the discharge of the medium through the discharge opening. Known media reservoirs have a substantially uniform cross-section and their wall thickness is matched to the requirements of the pumping device. Discharge devices which are designed for a limited number of pump strokes or lifts, particularly for one or two strokes, frequently have a sealed media reservoir. For this purpose the pumping device is designed in such a way that the medium to be discharged is only fed out of the media reservoir, which has been sealed up to this time, on performing the pump stroke. The pumping device during the first pump stroke opens the seal of the media reservoir and places the latter under pressure. Discharge devices of this type designed for a small number of pump strokes are more particularly used for the administration of inoculating agents. As the pumping device only has to be operated one or two times and the discharge device for hygienic reasons is then disposed of, there is a great interest in a particularly inexpensive, but reliable discharge device. The prior art discloses various solutions for this purpose and they have in particular a plastic media reservoir. A plastic media reservoir is in particular characterized by low manufacturing costs, but suffers from disadvantages with regards to long-term stability and sealing action. The storability of the stored medium is influenced both by diffusion processes and the quality of the sealing surfaces. These disadvantages are more pronounced with media reservoirs containing two different media, particularly a liquid medium and a solid medium. With such media reservoirs particularly high demands are made on the sealing area between the solid and liquid media. Only in this way is it possible to prevent a degeneration of the two separate constituents. Known solutions are unable to provide a completely satisfactory response.

The problem of the invention is therefore to provide a discharge device of the aforementioned type, which permits an improved mixing of several media and a good dosability of at least one medium for a discharge.

This problem is solved in that the media reservoir has at least two, mutually rigidly positioned media reservoir sections, which pass into one another in the interior thereof through a step shoulder. The media reservoir is subdivided into at least two media reservoir sections, which have different cross-sections and are positioned rigidly relative to one another by a fixed connection. The cross-section change between the two media reservoir sections occurs in the form of a step shoulder, which produces the transition between the at least two different cross-sections. With a particular planar surface the step shoulder bridges a sudden cross-section change between the two different cross-sections of the media reservoir sections. Thus, particularly in conjunction with at least one pump piston section associated with the media reservoir section, it is possible to bring about a precise dosing and a particularly good miscibility of the at least two media.

According to a development of the invention, the step shoulder has a sharp, circumferential edge. Between the media reservoir sections the sudden cross-section change is bridged by the step shoulder. At a transition point between the in particular areal step shoulder and the inner face of the media reservoir section having the smaller cross-section, the inner face of the media reservoir section penetrates the face of the step shoulder, the two faces passing into one another along a cutting edge. As a function of the design of the two previously described faces, said cutting edge is placed in a plane or in space and in particular with a cylindrical inner face and a planar step shoulder a planar, circular cutting edge is obtained, the two faces being in particular at an angle of 90ø to one another. A sharp edge between the two faces can in particular be implemented in an angular range of 20 to 135ø, preferably 80 to 110ø. The sharp edge ensures a particularly good seating of a sealing agent provided in this area. Moreover, as a result of the sharp edge, particularly when using the media reservoir for storing at least two different media, a particularly advantageous thorough mixing of the corresponding media results from the hydraulic characteristics of such an edge. A particularly precise dosing can be obtained when there is only a single medium.

According to a further development of the invention, the media reservoir sections are formed by two separate hollow bodies, which are superimposed over a portion of their length and which are tightly interconnected in the superimposing area. Through the construction of the media reservoir sections as separate hollow bodies, it is possible to use different media reservoir section materials for the media to be stored. Thus, the materials can in particular be matched to the needs of the particular medium. In order to create a unitary media reservoir the corresponding hollow bodies are superimposed over a portion of their length and tightly interconnected in the thus formed superimposing area.

According to a further development of the invention, at least one media reservoir section is produced from a crystalline or amorphous material and has an almost smooth inner wall. Crystalline and amorphous materials, particularly metals, ceramics or glasses, are particularly suitable for the long-term storage of media. As a result of their high density, they only allow an extremely small diffusion between the medium to be stored, the media reservoir material and the environment. In addition, such materials behave inertly with respect to the media to be stored. Even when the filled media reservoir is stored for a long time, there is only a limited risk of the medium interacting with the media reservoir material. Another advantage of such materials is that they can be manufactured with almost smooth inner walls by means of inexpensive, large quantity production processes. Thus, there is a marked reduction in the active surface for an interchange between the medium and the media reservoir section material. This also brings about a particularly advantageous seating of the sealing elements. Another advantage of a smooth inner wall becomes apparent during the discharge process, particularly if at least one media reservoir section is also used as a pump cylinder. A smooth inner wall contributes to a particularly low friction, efficient pumping movement of the pump piston, which is more particularly constructed as a sealing element.

According to a further development of the invention, an outer contour of the inner hollow body is at least stagewise matched to an inner contour of the outer hollow body. Through the matching of the outer contour of the inner hollow body to the inner contour of the outer hollow body, particularly when using ISO tolerance ranges, it is possible to bring about a reliable and advantageous fitting, as well as a reliable sealing action between the two media reservoir sections. Moreover and in particular when using an amorphous material such as glass, it is possible to ensure during the fitting of the media reservoir sections that no inner stresses and strains occur, which could bring about damage to the media reservoir sections or which could impair the sealing action of the superimposing area.

According to a further development of the invention, the at least two hollow bodies are integrally joined in the superimposing area and this can in particular be brought about by fusing, soldering or bonding the materials of the media reservoir sections. The fusion of the materials of the media reservoir sections more particularly takes place by the supply of thermal energy using an open flame, electric arc, frictional heat, laser light or induction. In soldering processes use is made of a filler material with a melting point below that of the melting points of the materials to be connected and which can be introduced into a capillary gap of the superimposing area by heating the media reservoir sections. For bonding the media reservoir sections use is more particularly made of a one or two-component adhesive, which can be activated and cured anaerobically, by external energy supply, by chemical reaction with a curing agent, by air or moisture contact or by further mechanisms.

According to a further development of the invention, at least the superimposing area of at least one hollow body is cylindrically shaped and in particular has a scarf joint. The cylindrical design of the superimposing area of at least one hollow body represents a particularly inexpensively producible geometry for a media reservoir section. Further advantages are associated with the connection to the adjacent media reservoir section. A cylindrical design avoids stress peaks in the media reservoir sections to be connected and consequently reduces the cracking and leaking risks. A scarf joint of the cylindrically shaped superimposing area of the media reservoir section is in particular brought about by a conical design of the superimposing area. At the front face facing the other media reservoir section, the cone has a smaller diameter and with increasing distance from the other media reservoir section a diameter increase takes place.

According to a further development of the invention, each media reservoir section has a chamber for in each case one medium which is separate from the adjacent media reservoir section. Thus, the media reservoir is able to store two completely different media, particularly in a liquid, solid or gaseous aggregate state, which are intermixed only at the time of discharge. For this purpose, level with the step shoulder, the media reservoir is separated into two chambers by means of a sealing element. Particularly as a result of the sharp, circumferential edge associated with the step shoulder, as well as the almost smooth inner wall of at least one media reservoir section, a particularly advantageous sealing action is obtained. During a discharge process said sealing element is moved from a sealing position more particularly into one of the chambers of the media reservoir and as a result the desired thorough mixing of the at least two different media in the media reservoir takes place. The media mixture can then be delivered through the discharge opening to the environment. As a result of the sharp edge of the step shoulder the mixing action is assisted and can therefore be ensured in a short time period. As a function of the particular application, it is possible to provide both liquid and solid media in the media reservoir sections and which as a function of the mixing ratio can be introduced into the media reservoir sections whose volumes have been correspondingly adapted.

According to a further development of the invention on an inner wall of a media reservoir section facing the media chamber in at least one sealing area is provided a circumferential shape for receiving an at least stagewise spherical sealing element. Such sealing elements are in particular made from elastomeric materials and, particularly during sealing fitting, offer advantages compared with areal sealing elements with a cylindrical cross-section. This in particular results from the spherical shape, which permits an easy introduction of the sealing element into the shape provided in the sealing area. An at least stagewise spherical sealing element is virtually neutral with respect to an orientation relative to the sealing area. The circumferential shape in the sealing area on the inner wall of the media reservoir section can in particular be in the form of a groove or projection arrangement. The at least stagewise spherical sealing element engages stagewise and positively in the sealing area.

According to a further development of the invention, as hollow bodies are provided concentrically positioned, cylindrical glass tube sections, which are in particular laser welded together in the superimposing area. Glass tube sections can be industrially inexpensively produced with extremely precise cross-sections and can be obtained in virtually random quantities. An individual adaptation of the cylindrical glass tube sections in the superimposing area during fitting is unnecessary in view of the high accuracy to size and low tolerances of such hollow bodies. This makes it possible to bring about a particularly good superimposing of the media reservoir sections with extremely limited additional costs. By making the media reservoir from cylindrical glass tube sections, this brings about on a long term basis an extremely good sealing action, both with respect to the sealing elements in the superimposing area and with respect to the sealing elements located frontally on the hollow body ends. The integral joint between the media reservoir sections can in particular be produced in gastight manner with high process reliability using laser welding. The production of this joint also has no effect on the accuracy to size of the media reservoir, because when using a laser welding process only the outer marginal zones of the media reservoir sections to be joined together are melted. The inner areas of the cylindrical glass tube sections are not subject to a melting action and therefore suffer no deformation. This feature can be advantageously combined with that of a scarf joint.

According to a further development of the invention, on the pumping device is provided at least one force-limited retention device, which prevents a pump stroke below a defined force level. In order to prevent an undesired actuation and an inadequate pressure build-up in the media reservoir, a force-limited retention device is provided on the pumping device. For a pump stroke the user must place the discharge device under pressure, particularly by the force of a finger. Only on exceeding a previously defined force level is the pump stroke released by the retention device, so that as a result of the inertia of a system formed by the discharge device and the fingers of the user, it is not possible to drop below a clearly defined pump stroke speed. Force-limited retention devices can in particular be implemented in the form of locking or stop edges or tear-off elements.

According to a further development of the invention, there are force-limited retention devices with different locking forces for a clearly defined sequence of individual pump stroke steps. Through such force-limited retention devices, it is possible to ensure that a planned operating sequence in the discharge device is precisely respected and consequently the thorough mixing of the different media necessary in the case of media reservoirs with two or more separate chambers takes place correctly. The different locking forces are implemented by a different design of the retention devices and in particular by combining a locking edge with a tear-off element a reliable differentiation of different locking forces can be obtained. This leads to a planned, controlled pump stroke sequence. In particular, the locking force of the retention device in the form of a locking edge is firstly overcome and is completed by one or more steps of a first pump stroke phase. Only subsequently is the locking force of the retention device in the form of a tear-off element exceeded and a second discharge stroke phase completed.

Further advantages and features of the invention can be gathered from the claims and the following description of a preferred embodiment of the invention with reference to the attached drawings, wherein show:

FIG. 1 A view of a diagrammatic sectional representation of a discharge device with a media reservoir.

FIG. 2 A sectional representation of a second embodiment of a discharge device with a media reservoir.

FIG. 3 A sectional representation of a media reservoir of the second discharge device embodiment.

A discharge device 1 diagrammatically shown in FIG. 1 has a body 2, which incorporates all the further components of the discharge device or at least stagewise encircles the same. At an end located in the discharge direction 33 the body 2 has a nozzle shaft 11, as well as a discharge opening in the form of a nozzle 10. In the present embodiment the nozzle shaft 11 is in particular in the form of a nose olive and has a substantially rounded, conical section-like contour. At an end remote from the discharge direction 33 the body 2 is equipped with an at least stagewise circumferential finger rest 13. The finger rest 13 is provided in order to bring about a relative movement between the body 2 and a pressure sleeve 5, particularly as a support surface for an index finger and middle finger of a user. For producing the force necessary for a pump stroke, the thumb of the user is placed on a base surface 14 of the pressure sleeve 5. This permits a force flow between the finger rest 13, body 2, further components of the discharge device 1 and the hand of the user. The pump stroke and therefore the discharge of the medium or media is brought about by the relative movement between the body 2 and the pressure sleeve 5.

The pressure sleeve 5 is positively locked in the interior of the body by means of an outer locking cone 22, which on fitting the discharge device is shoved through a flexible inner locking cone 23 of the body 2. The positive engagement of the pressure sleeve 5 prevents a disassembly from the body 2. Movement of the pressure sleeve 5 in the discharge direction 33 is not limited by the positive engagement between pressure sleeve 5 and body 2. During the discharge movement, the outer locking cone 22 of the pressure sleeve 5 is guided along a guide bush 29 of the body 2 and consequently permits a straight movement of the pressure sleeve 5 relative to the body 2. The pressure sleeve 5 has a substantially cup-shaped cross-section and on the bottom of the cup-shaped cross-section is provided a centrally positioned solid ram 15 passing out of the bottom surface. The solid ram is in a rest position of the pressure sleeve 5 directly in engagement with an outer seal 8 of the solid reservoir 6.

The solid reservoir 6 is a media reservoir section produced from a cylindrical glass tube section and which is connected in gastight manner by means of a superimposing area 31 and a connecting area 27 in the form of a laser weld to a further media reservoir section in the form of a liquid reservoir 4. The solid 17 stored in the solid reservoir 6 is separated by an inner seal 7 provided in the discharge direction on a front face of the solid reservoir 6 spaced from the outer seal 8, from a liquid medium 16 contained in the liquid reservoir 4. The inner seal 7 is supported on a cylindrical surface 35 of the solid reservoir 6 acting as a sealing surface. On the front face of the solid reservoir 6 is also provided a media reservoir edge 32 resulting from the cross-section difference between the liquid reservoir 4 and solid reservoir 6 and located at an inner area of the step shoulder 34. The solid reservoir 6 is jointed in the liquid reservoir 4, which cannot be gathered from the drawing.

The liquid reservoir 4 stores a liquid medium 16, which is sealed by a piston packing 3 at a front face facing the discharge opening 10. The piston packing is supported on a cylindrical surface 24 of the liquid reservoir 4 and as a result of its geometry and the limited roughness of the cylindrical surface 24 can be easily displaced during the discharge process. Immediately above the piston packing 3 the riser pipe 9 is engaged in the body 2, being supported by a liquid ram 18 in a portion of the body 2 facing the media reservoir and which is provided on its front face facing the media reservoir with a riser pipe cutting edge 19.

Before a pump stroke can be performed, by applying a force between the finger rest 13 and the pressure surface 14, the user must exert a minimum pressure defined by the force-limited retention device in the form of a locking edge 20. Only after overcoming the locking edge 20 is it possible for there to be a discharge movement of the pressure sleeve 5 and the media reservoir relative to the basic casing. At the start of the discharge stroke the riser pipe cutting edge 19 cuts through a tapered area of the piston packing 3. As soon as the riser pipe 9 has completely penetrated the piston packing 3 and is embraced all-round by it, the liquid ram 18 with its piston pressure surface 26 comes into contact with the piston packing 3 and places the media reservoir under pressure by means of the force exerted by the user. As a result of the force exerted by the user, at the same time the solid reservoir 6 is also placed under pressure by the force on pressure surface 14 transferred via solid ram 15 to outer seal 8. As a result, the inner seal 7 is shoved into the liquid reservoir 4 and brings about a complete mixing of solid medium 17 and liquid medium 16. In the present embodiment the discharge device 1 is in the form of a disposable device, i.e. the media 16, 17 stored in the media reservoir chambers are intermixed by a single pump stroke and by the discharge device nozzle 10 are delivered through the media channel 12 of riser pipe 9 in discharge direction 33.

Diverging from the discharge device shown in FIG. 1, FIG. 2 shows an actual embodiment of the discharge device 1a. In the following description details are only provided concerning the differences compared with FIG. 1. In the case of the discharge device 1a shown in FIG. 2, between the body 2a and pressure sleeve 5a is provided an additional intermediate sleeve 37a. On an inner guide face 38a, the intermediate sleeve 37a is provided on an end facing the pressure sleeve 5a with a locking recess 39a, which together with a locking collar 40a of the pressure sleeve 5a forms a first, positively acting, force-limited retention device. On a side facing the body 2a, the intermediate sleeve 37a is provided with a circumferential collar web 41a, which has an inner locking cone 23a. The inner locking cone 23a forms with the outer locking cone 22a a positive connection, which is produced on fitting the discharge device 1a and serves for holding the media reservoir in body 2a and which also forms a second, force-limited retention device. The limitation of the actuating force of this second force-limited retention device is implemented by the collar web 41a in the form of a tear-off ring.

In order to perform a pump stroke, in the case of the discharge device 1a of FIG. 2 and in the same way as with the discharge device 1 of FIG. 1, a force is exerted on the discharge device 1a between the finger rest 13a and the pressure face 14a of the pressure sleeve 5a. As soon as the user applies an adequate pressure force to the pressure face 14a, a locking force determined by the geometry of the locking recess 39a, as well as the locking collar 40a and the corresponding material characteristics can overcome this force-limited retention device. Thus, the pressure sleeve 5a moves in discharge direction 33a and slides along the inner guide face 38a in intermediate sleeve 37a. Through the solid ram 15a provided on the pressure sleeve 5a the outer seal 8a is moved in discharge direction 33a, so that there is a pressure build-up in solid 17a in solid reservoir 6a. This built-up pressure is propagated through the solid 17a, inner seal 7a and liquid medium 16a to the piston packing 3a. The piston packing 3a is only held in fixed manner by static frictional forces and can be displaced in the discharge direction 33a by overcoming said forces. Thus, simultaneously there is a synonymous movement of outer seal 8a, solid 17a, inner seal 7a and liquid medium 16a. As soon as the inner seal 7a with its sealing area has passed the media reservoir edge 32a, there is an intermixing of the solid 17a with the liquid medium 16a. Through the displacement of the piston packing 3a in the discharge direction 33a, the latter is penetrated by the riser pipe cutting edge 19a. Shortly before the riser pipe 9a has completely penetrated the piston packing 3a, a stop collar 42a of the pressure sleeve 5a engages positively on a front face 43a of the intermediate sleeve 37a facing the pressure sleeve 5a. Thus, initially there is no further pressure build-up in the mixture of liquid medium 16a and solid 17a and the riser pipe 9a is still not in contact with the mixture in the media reservoir. Only on overcoming a minimum actuating force leading to a tearing off of the collar web 41a from the intermediate sleeve 37a, is the piston packing 3a completely penetrated by the riser pipe 9a and the intermediately formed mixture of liquid medium 16a and solid 17a can escape in sudden bursts into the environment through media channel 12a. The liquid ram 18a with its piston pressure face 26a acts on a front face of the piston packing 3a facing the nozzle 10a and places under pressure the mixture largely located in the liquid reservoir 4a until a front stop face 25a of the liquid reservoir 4a runs up onto a not shown stop in the body. Thus, the pump stroke is at an end and the mixture of liquid medium 16a and solid 17a has been discharged, apart from a residual quantity.

The media reservoir, which is not further designated and which is shown in FIG. 3 comprises a cylindrical glass tube with a frontally arranged, outwardly directed, circumferential collar, which has a precisely determined external diameter on a guide face 21b provided centrally with respect to a cylinder centre axis. On an inwardly facing cylindrical surface 24b of the liquid reservoir 4b is provided an insertion cone 44b, which narrows from a front stop face 25b of the liquid reservoir 4b to a not designated internal diameter of the liquid reservoir 4b. On the front face of the liquid reservoir 4b remote from the circumferential collar is provided a stagewise, exactly determined internal diameter, which is provided for receiving a solid reservoir 6b in the form of a cylindrical glass tube. The solid reservoir 6b, which at least stagewise has an external diameter precisely matched to the internal diameter of the liquid reservoir 4b, forms together with the latter a superimposing area 31b. On a not further designated step formed by the diameter difference between liquid reservoir 4b and solid reservoir 6b is provided a joining area 27b, which in particular results from the laser welding of the two cylindrical glass bodies. On a front face of the solid reservoir 6b facing the liquid reservoir 7b is provided a sharp-edged step shoulder 34b, which also results from the diameter difference between liquid reservoir 4b and solid reservoir 6b.

Other variants of the discharge device according to the invention can be implemented as double or multiple dosing systems. This does not lead to functional areas essential to the invention being changed.

What is claimed is:

1. Discharge device for at least one medium with a media reservoir, a pumping device and a discharge opening wherein the media reservoir has at least two media reservoir sections positioned rigidly with respect to one another and which pass into one another in their interior through a step shoulder, wherein first and second force-limited retention devices with different locking forces receive an applied force from the pumping device and when the value of the applied force exceeds the locking force of the first force-limited retention device, the media reservoir sections open with respect to each other to mix the media, and subsequently, when the applied force exceeds the locking force of the second force-limited retention device, the media is discharged from the discharge opening.

2. The discharge device according to claim 1, wherein the step shoulder has a sharp, circumferential edge.

3. The discharge device according to claim 3, wherein the media reservoir sections are formed by two separate hollow bodies, which are superimposed over a portion of their length and which are tightly interconnected in the superimposing area.

4. The discharge device according to claim 1, wherein at least one said media reservoir section is made from a crystalline or amorphous material and has an almost smooth inner wall.

5. The discharge device according to claim 3, wherein an outer contour of an inner one of said hollow bodies is at least matched to an inner contour of said outer hollow body.

6. The discharge device according to claim 3, wherein the at least two hollow bodies are integrally joined in the superimposing area.

7. The discharge device according to claim 3, wherein at least the superimposing area of at least one said hollow body is cylindrically shaped and has a scarf joint.

8. The discharge device according to claim 3, wherein each said media reservoir section has a chamber separate from the adjacent media reservoir section for storing in each case one medium.

9. The discharge device according to claim 3, wherein at least one sealing area is provided on an inner wall of one of said media reservoir sections facing respective media chambers with a circumferential shape for receiving an at least stagewise spherical sealing element.

10. The discharge device according to claim 3, wherein concentrically arranged, cylindrical glass tube sections comprise the hollow bodies and which are laser welded together in the superimposing area.

11. The discharge device according to claim 1, wherein the pumping device comprises a single stroke pumping device operating with a single stroke, and wherein the force-limited retention devices with the different locking forces provide a clearly defined sequence of individual pump stroke steps that in combination provide the single stroke of the pumping device.

12. A discharge device comprising:
a main body;
a media reservoir with at least two sealed media reservoir sections positioned rigidly with respect to one another and passing into one another in their interior through a step shoulder, the media reservoir including a sealing element separating mediums in the reservoir sections, the media reservoir being at least enclosed in part by said main body;
a discharge opening at a first end of the main body; and
a single stroke pump device at least partially enclosed by the main body and projecting from a second end of the main body for applying a first linear force in a first direction to open the sealing element so that the mediums in the two media reservoir sections nix during a first mixing stage, said single stroke pump device for applying a second linear force in the first direction during a second discharge stage to discharge the mediums from the discharge opening,
wherein a single stroke of the pump device in the first direction by applying the first linear force and the second linear force mixes end discharges the mediums, whereby operation of said discharge device is free from movement of the pump device in a second direction opposite from the first direction.

13. The discharge device according to claim 12, wherein said reservoir sections are formed by two separate hollow bodies which are superimposed over a portion of their length and are tightly connected in the superimposed area.

14. The discharge device according to claim 13, wherein each said media reservoir section stores a different medium, one medium comprising a liquid and The other medium comprising solids.

15. The discharge device according to claim 12, including a force-limited retention device to oppose movement of the pump device until the second linear force exceeds a predetermined value that fractures the retention device.

16. The discharge device according to claim 12, wherein said sealing element comprises a first sealing element and said discharge device includes a second sealing element at a second end of a first one of said media reservoir sections,
wherein said pump device comprises a pressure sleeve including at a first end an outer locking cone for locking the first end or said sleeve within the main body, and a ram projecting onwardly from a second outer end of said pressure sleeve for contacting the second seal located at the second end of the first one of said media reservoir sections,
wherein said main body includes a locking edge that limits movement of said liquid reservoir toward said nozzle until the second linear force is applied thereto, and
wherein said discharge device comprises a third sealing element at an end of a second one of said media reservoir sections and further comprises a pipe having a cutting edge for cutting said third sealing element to provide a flow path therethrough from said media reservoir to said discharge opening.

17. The discharge device according to claim 12, wherein said pump device comprises a pressure sleeve for applying the first linear force in the first direction against a first retention device to open the sealing element so that the medium in the two media reservoir sections mix during the first mixing stage, and for applying the second linear force in the first direction against a second retention device during the second discharge stage to discharge the mixed media from the discharge opening.

18. The discharge device according to claim 17, wherein the first retention device comprises a locking collar and the second retention device comprises a breakable collar web, wherein said sealing element comprises a first sealing element and said discharge device includes a second sealing element located at an end of a second one cit said media reservoir sections, said discharge device further comprising a pipe having a cutting edge for cutting said second sealing element to provide a flow path therethrough from said media reservoir to said discharge opening.

* * * * *